United States Patent [19]

Hjerten et al.

[11] Patent Number: 5,114,551
[45] Date of Patent: May 19, 1992

[54] MULTI-POINT DETECTION METHOD FOR ELECTROPHORESIS AND CHROMATOGRAPHY IN CAPILLARIES

[75] Inventors: Stellan Hjerten; Tasanee Srichaiyo, both of Upsala, Sweden

[73] Assignee: Bio-Rad Laboratories, Inc., Hercules, Calif.

[21] Appl. No.: 769,073

[22] Filed: Sep. 30, 1991

[51] Int. Cl.$^5$ .................... B01D 57/02; B01D 61/42; C25D 13/00
[52] U.S. Cl. ............... 204/180.1; 204/299 R; 204/182.8; 356/344; 436/161; 73/23.4; 73/61.52; 210/656; 210/198.2
[58] Field of Search ............ 204/299 R, 180.1, 182.8; 356/344; 436/161; 210/656, 198.2; 73/61.1 C, 23.4

[56] References Cited

U.S. PATENT DOCUMENTS

| | | | |
|---|---|---|---|
| 3,623,812 | 11/1971 | Hanning | 356/344 |
| 3,676,649 | 7/1972 | Burk | 73/61.1 C |
| 4,353,242 | 10/1982 | Harris et al. | 73/61.1 C |
| 4,592,842 | 6/1986 | Tomlinson | 210/198.2 |
| 4,859,301 | 8/1989 | Brenner et al. | 204/180.1 |
| 4,909,920 | 3/1990 | Sarrine et al. | 204/182.8 |
| 4,985,129 | 1/1991 | Burd | 204/299 R |

OTHER PUBLICATIONS

Beckers, "Use of a Double-Dectector System for the Measurement of Mobilities in Zone Electrophoresis", J. of Chrom, 452 (1988) 591–600.

*Primary Examiner*—John Niebling
*Assistant Examiner*—Caroline Koestner
*Attorney, Agent, or Firm*—Townsend and Townsend

[57] ABSTRACT

Multiple electropherograms or chromatograms representing successive stages of an electrophoretic or chromatographic separation in a capillary are obtained by training a recorder on a succession of detection windows in the capillary, spaced apart along the capillary length. A single immovable detector is used, and the capillary is either held such that each detection window is placed in alignment with the detector in succession, or is looped such that the detection windows all lie in the path of the detector at the same time.

20 Claims, 4 Drawing Sheets

MULTI-POINT DETECTION METHOD FOR ELECTROPHORESIS AND CHROMATOGRAPHY IN CAPILLARIES

This invention lies in the fields of capillary electrophoresis and capillary chromatography, and in particular relates to methods of on-line detection.

BACKGROUND OF THE INVENTION

Capillary electrophoresis and capillary chromatography provide a number of distinct advantages as separation processes for biochemical mixtures. One advantage is the small volume of the capillary interior. This permits one to perform separations on extremely small samples, and at high speed. Another advantage, which pertains specifically to electrophoresis in capillaries, is the rapid rate at which heat is dissipated outward from a capillary due to the capillary's narrow bore. This permits the use of a high voltage to drive the electrophoresis, which provides separations at high speed and efficiency. Each of these advantages renders capillaries particularly useful for analyzing samples of biological interest, particularly mixtures of peptides, proteins and nucleic acids.

The most advantageous method of detecting separated solutes in capillary separations is on-line detection. One of several advantages which on-line detection offers is the capability of obtaining a multitude of chromatogram and electropherogram traces during the course of a single continuous electrophoretic separation. The most common method of achieving this is by scanning the capillary several times while the separation is in progress. This permits the operator to follow the course of a separation, to determine solute mobilities and peak areas on the basis of several measurements rather than just one, and to select a chromatogram and an electropherogram which has the greatest peak separation with the least broadening.

One difficulty with scanning is the need for either a moving detector or a moving capillary, and the need to accurately correlate the relative positions of the detector and capillary with the peaks observed. Another difficulty is the need to use a capillary made of quartz which is ground and polished both inside and outside to minimize variations in internal diameter and wall thickness which might otherwise produce baseline fluctuations. A third difficulty is the need for both the capillary and the medium inside the capillary to be transparent to a detection beam such as ultraviolet (UV) light, along the entire length of the capillary along which scanning will be performed. In many cases, coatings are applied to the outer walls of capillaries for purposes of rendering the capillary more flexible and less prone to breakage. Many of these coatings are opaque to UV light, and thus do not permit scanning.

The use of two detectors mounted at a fixed distance from each other is disclosed by Beckers, J.L., et al., "Use of a Double-Detector System for the Measurement of Mobilities in Zone Electrophoresis," *J. Chromatog.* 452: 591–600 (1988). Such a system is less than fully satisfactory, however. The equipment cost for a two-detector system of course includes the cost of two detectors, which are a major component of the cost of the system as a whole. Also, two detectors seldom have the same sensitivity, and differences in sensitivity will result in different peak areas for a particular solute. Still further, the use of two detectors imposes restrictions on how the detectors may be positioned relative to each other, i.e., there is a limit to how closely they can be placed unless they utilize fiber optics.

These and other problems are addressed by the present invention.

SUMMARY OF THE INVENTION

A method has now been developed by which multiple chromatograms and electropherograms representing successive stages of a chromatographic or an electrophoretic separation in a capillary can be obtained without longitudinal scanning of the capillary and without the need for multiple detectors. In accordance with this invention, variations in light absorptivity as a function of time are detected at a plurality of locations spaced apart along the length of the capillary, with but a single detector. This is achieved in one of two ways.

In the first, a detection window in the capillary is aligned with the detection beam of a detector, the window being one of several detection windows positioned at intervals along the length of the capillary. Once all solute peaks have passed the detection window, and have thus been detected by the detector, the capillary is moved backward, in the direction opposite the direction of migration of the solutes, to align the next detection window with the detector beam. This is repeated a sufficient number of times until all such detection windows have been placed in the detector beam and solute peaks passing through the capillary at the location of each window have been detected.

In the second, the capillary contains a plurality of detection windows positioned at intervals along its length, as in the system described in the preceding paragraph. The capillary is looped between these detection windows, however, with each adjacent pair of detection windows separated by at least one loop. The loops are arranged such that the detection windows are all located sufficiently close to each other to fall within the path of a single detector beam. The loops may all be in the same direction whereby solutes pass the beam in the same direction each time, or the loops may alternate in direction whereby solutes pass the beam in alternating directions from one loop to the next, or the loops may be a combination of both. In any case, continuous detection records all peaks passing through all detection windows, and the order in which the peaks are detected serves as a means of identifying the detection window through which any particular peak was detected.

In either method, average peak areas for each component of the sample mixture can be obtained by simply averaging the areas of corresponding peaks among the various chromatograms or electropherograms, and the mobility of each component can be determined to a high degree of accuracy by plotting the distances from the injection end of the capillary to each window vs. the times at which the peaks are detected in the window. Other features and advantages of the invention will become apparent from the description which follows.

DETAILED DESCRIPTION OF THE INVENTION AND PREFERRED EMBODIMENTS

Figure 1:
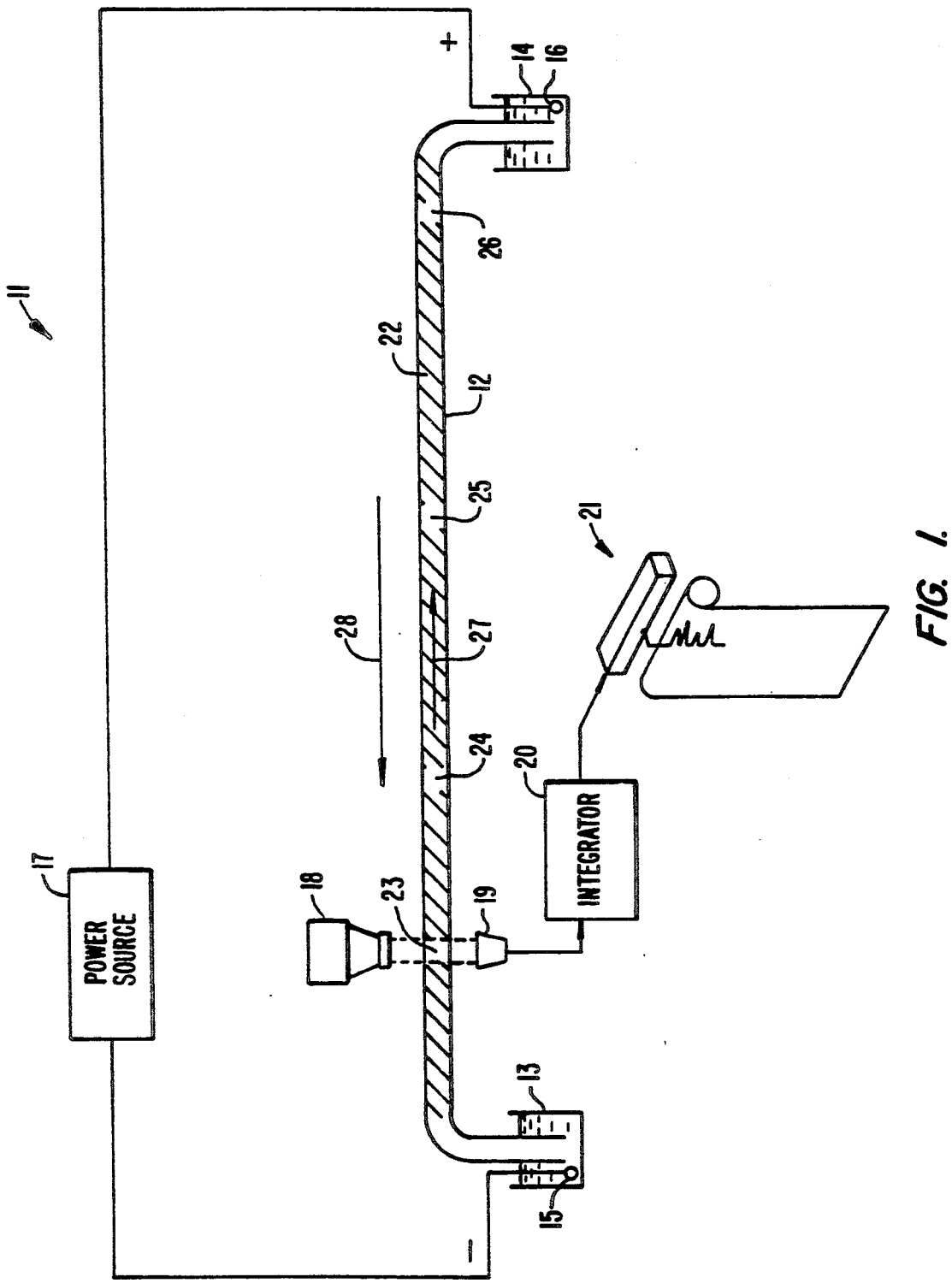
FIG. 1 is a diagram of one example of an electrophoresis system implementing the present invention.

Capillary tubes for use in the present invention may be of any material in which electrophoresis and chromatography may be performed without interference from the material itself, and in which detection windows may be incorporated, or in which short segments may be designated as detection windows, at specified distances along the capillary length. The detection windows will be of any composition or construction which will permit the passage of a detection beam, and will accordingly be selected or adapted in accordance with the type of beam and detection system used, which will in turn depend on the nature of the solutes being separated. Detection systems based on absorption of UV light are the most common and are particularly convenient for use in capillary electrophoresis of biological mixtures such as small peptides, proteins and nucleic acids. The detection windows for such systems will therefore be transparent to UV light.

Since UV light transparency for such systems is required only of the detection windows, the invention may be implemented using capillary tubes other than quartz. The segments of the capillary tube between the detection windows may in fact be of any material which is inert and does not interfere with the separation. This includes, for example, glass and other silica-containing materials, plastics, and metals such as stainless steel. Capillaries which are the easiest and the least expensive to construct will be those in which the entire capillary is constructed of the same material, however. A particularly convenient example is fused silica.

Fused silica capillaries are generally supplied with a polyimide coating on the outer capillary surface to enhance its resistance to breakage. Since the polyimide coating is not transparent to UV light, a detection window may be formed by removing the coating to leave a narrow band of exposed fused silica surface sufficiently wide to permit the passage of enough of the detection beam to achieve a reading. In a capillary of approximately 0.1 mm inner diameter or less, the band may be from about 0.01 mm to about 1.0 mm in width. Removal of the coating may be achieved by conventional means, an example of which is oxidation by a heated probe such as an electrified wire. Coatings which are transparent to UV light do not require removal. Fused silica tubing with such a coating is available from Polymicro Technologies Inc., Phoenix, Ariz., U.S.A.

When treatments of the internal wall surface of the capillary are desired for purposes of suppressing adsorption and, in the case of electrophoresis, electroendosmosis, treatment agents which do not interfere with the detection beam may be used. A treatment agent of this type may be selected from the various materials known among those skilled in the art for use in suppressing adsorption and electroendosmosis, and will generally be a monolayer of a low molecular weight compound or of a polymer, examples of which are linear polyacrylamide, dextran and methyl cellulose. The treatment agent may be deposited by conventional methods well known in the art of manufacturing capillaries. The use of a treatment agent is optional, however; the invention extends to capillaries which are not internally coated as well as to those which are.

The number of detection windows used in a single capillary is not critical and may vary widely. The number will be at least two, and for most applications will be no more than six. Capillaries with three to five detection windows are preferred. In some cases, the number of detection windows will be limited by the length of the capillary and by the need to space the windows sufficiently far apart to permit all solutes to pass one window before reaching the next, as explained further below.

The arrangement, number and spacing between the detection windows is not critical and may vary widely. The most convenient and most easily interpreted results, however, will be obtained when the solute peaks are detected in discrete non-overlapping groups, i.e., chromatograms or electropherograms, each such group corresponding to a single detection window. Preferably, therefore, the detection windows will be spaced far enough apart that a continuous detector trace from one detector will show all chromatograms or electropherograms in succession with no overlap. If an overlap indeed occurs between the last two or three chromatograms or electropherograms, the peaks and the sequence in which they are detected may still be identified provided the overlapping peak sequences are preceded by at least one, and preferably two, non-overlapping peak sequences. Relative retention times determined from these early non-overlapping peak sequences may then be used to sort out the later peak sequences and identify the corresponding peaks.

The detection windows may be positioned at equal intervals or at successively increasing intervals, the choice depending on the range of mobilities among the solutes. For solute mixtures in which the time required for all solutes to pass any one detection window is small compared to the time required for a given solute to migrate from one detection window to the next, the detection windows are preferably spaced at equal intervals from each other. For solute mixtures in which the spread of the peaks increases greatly as the peaks migrate from one end of the capillary to the other, the spacing between the detection windows preferably increases in the direction of migration so that each successive detection window can accommodate the ever increasing width of the peak spread before the peak spread reaches the next window.

One can minimize the occurrence of fluctuations of drift in the baseline of the recorder used for detecting the solutes passing each detection window by imposing temperature control over such elements of the system as the capillary (in the regions of the detection windows) and the detector. This is readily achieved by the use of circulating coolants, fans, heating jackets or mantles, or other similar measures which will readily occur to those skilled in the art, used in conjunction with thermostats or equivalent temperature control devices. This will avoid minute variations in the relative positions of the light beam, the detection windows and the photodiode.

The size of the capillary in terms of both length and internal diameter is not critical, and the invention extends to a wide range of capillary sizes, including microcapillaries. In general, capillaries will range from about 5 to about 300 microns in internal diameter, with about 20 to about 100 microns preferred. The length of the capillary will generally range from about 100 mm to about 3000 mm, with about 300 mm to about 1000 mm preferred.

For electrophoretic separations, the voltage used is likewise not critical to the invention, and may vary widely. Typical voltages range from about 500 V to about 30,000 V, preferably from about 1,000 V to about 10,000 V.

The separation medium is likewise not critical to the invention, and may be either liquid, gel or granules (such as beads for example), depending on the type of separation being performed. The separation medium may be one which permits the passage of a detection beam, and may accordingly be continuous through the detection windows as well as the segments of the capillary between the detection windows. Alternatively, the separation medium may be one which does not permit beam passage, and may accordingly contain gaps at the detection windows for the beam to pass through. This will most often occur in chromatographic separations, particularly where granules are used as the separation medium. In electrophoretic separations, conventional liquid buffer solutions are most commonly used, although the optimal choice for any particular run will depend on the nature of the solutes being separated.

In general, the separation, either chromatography or electrophoresis, may be conducted in accordance with conventional techniques, with materials and procedures known to be useful or adaptable to capillary separations. This extends to the methods of introducing the sample into the capillary prior to the separation, of running the separation, of maintaining temperature control, of performing on-line detection, and of processing or interpreting the results.

As indicated above, detection is preferably based on UV light absorption, but here again any type of on-line detection through a capillary tube may be used. Absorption of light is preferred for reasons of convenience and simplicity, but the wavelength at which absorption is measured may vary over a wide range. Once again, selection of the optimal wavelength will depend on the absorptivity of the solutes relative to the separation medium. Conventional detection equipment of the type commonly used for capillary chromatography or electrophoresis systems may be used.

The size of the detection beam (area of the beam cross section) relative to the diameter of the separation medium (i.e., the inner diameter of the capillary) will in many cases affect the degree of drift observed in the baseline of the signals detected. When a detector such as a photodiode is used, small changes or variations in position of the capillary relative to the photodiode or to the light beam may have a significant effect on the sensitivity of the detection. This effect may be minimized or eliminated by temperature control using a thermostat, since the photodiode, the capillary and the light beam may change their positions upon a change in temperature. The effect may also be minimized or eliminated by using a light beam which is larger than the inner diameter of the capillary, i.e., of a greater dimension in the direction transverse to the longitudinal axis of the capillary. In preferred embodiments of the invention, therefore, the transverse dimension of the detection beam will be from about 1.1 times to about 3.0 times the inner diameter of the capillary, preferably from about 1.3 times to about 1.8 times.

Figure 2:
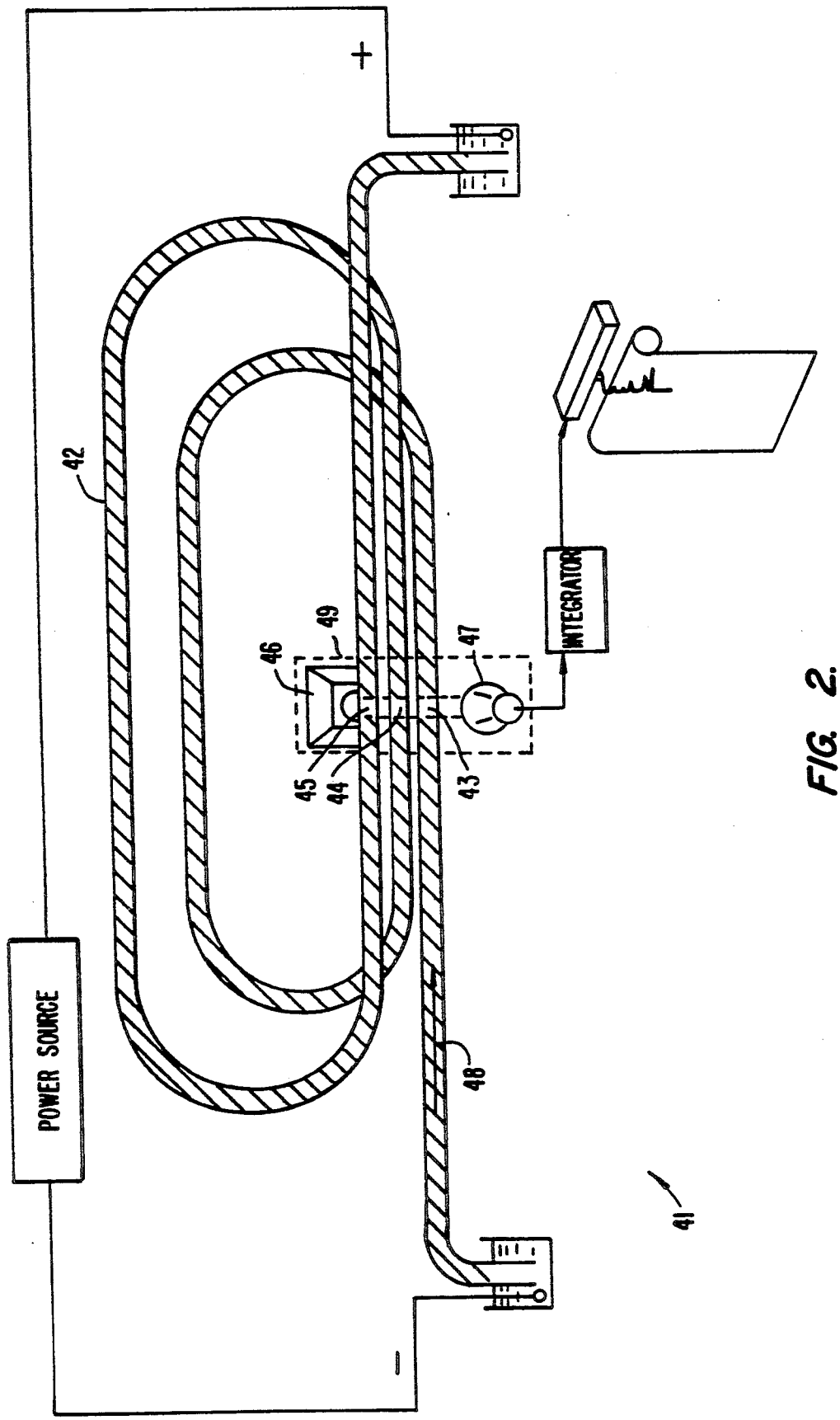
FIG. 2 is a diagram of a second example of an electrophoresis system implementing the present invention.
Figure 3:
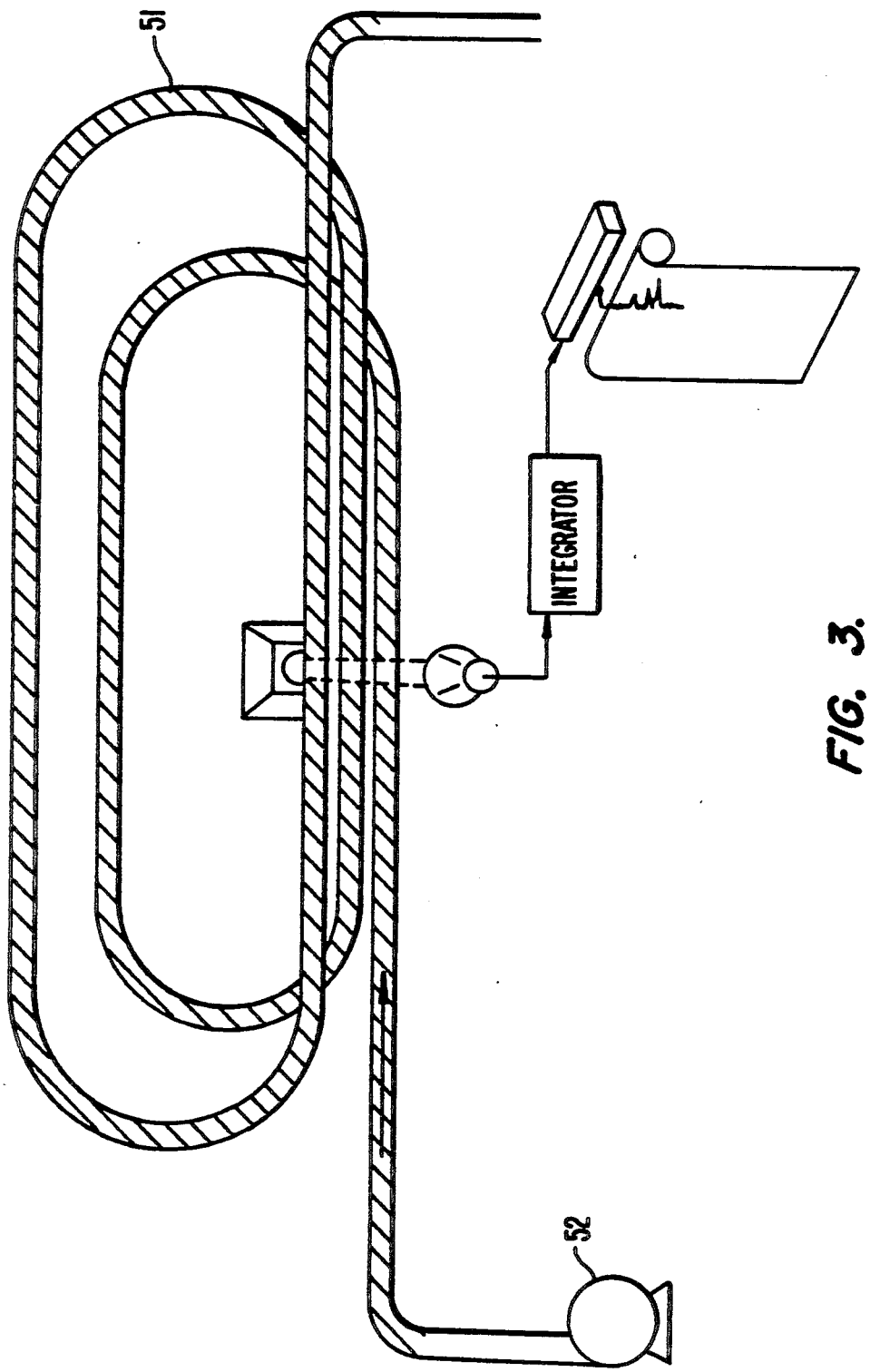
FIG. 3 is a diagram of an example of a chromatography system implementing the present invention.

Turning now to the drawings, FIGS. 1, 2 and 3 are representative sketches of the embodiments referred to above which exemplify the implementation of the present invention. The drawings are intended merely as illustrations of the invention as a whole.

In FIG. 1, an electrophoresis system 11 with a linear capillary 12 is depicted. The components of the system are the capillary 12, electrode reservoirs 13, 14, electrodes 15, 16, a power source 17, a UV light source 18, a photo diode detector 19, an integrator 20 and a recorder 21. The capillary 12 in this example is fused silica, and the outer surface of the capillary is coated with polyimide 22, represented in the drawing by dashed lines. The polyimide coating is discontinuous, leaving four short uncoated segments 23, 24, 25, 26 which are transparent to UV light and serve as detection windows. The migration of solutes occurs in the direction of the arrow 27. In the arrangement shown in the drawing, the system components are positioned for the detection of solutes at the first detection window 23. Once all solutes have passed that window, the capillary 12 is moved in the direction of the arrow 28 relative to the UV light source 18 and the photo diode detector 19 until the second detection window 24 is aligned with the light source and photo diode. Once all peaks passing the second detection window have been recorded, the capillary 12 is moved once again in the same direction, to place the third and fourth windows in succession in alignment with the light source and detector. Movement of the capillary may be accomplished manually or by an appropriate drive mechanism of conventional construction, timed either in a preset manner or in coordination with signals from the recorder indicating that a predetermined number of peaks has been detected.

FIG. 2 depicts an electrophoresis system 41 with a looped capillary 42 which is maintained stationary. The capillary is of fused silica as before, with the outer surface coated with polyimide except for three detection windows 43, 44, 45. All three windows are aligned however with the UV light source 46 and photo diode detector 47, such that no movement of any of the system components is necessary to obtain readings from all three windows. The segments of tubing which include the detection windows may be arranged in a bundle, or in a planar arrangement, and the planar arrangement may be transverse to the detection beam such that the beam passes through all windows simultaneously, or it may be parrallel to the detection beam such that the beam passes through the windows serially. All remaining parts of the system are identical to corresponding parts of the system of FIG. 1. The direction of migration of the solutes during electrophoresis is indicated by the arrow 48.

Temperature control to avoid base line drift and fluctuations is achieved by a system of temperature control units and thermostats. These are indicated by the dashed lines 49 in FIG. 2.

The invention also offers a benefit to electrophoretic separations of samples in which several of the sample components migrate very slowly relative to the others. In conventional practice, separations of this type generally require two experiments, one under conditions promoting a slow migration rate suitable for the more mobile components, and the other under conditions promoting a fast migration rate suitable for the less mobile components. By application of the present invention, however, two detection windows may be used, one close to the injector end of the capillary and the other relatively far from the injector end. With such an arrangement, the length of time required for all components to be detected is lessened considerably, since detection of the faster migrating components will be recorded only when these components pass the detection window furthest from the injector end, while detection of the slower migrating components will be recorded as they pass the detection window nearest the injector end. In this embodiment of the invention, it is not necessary for either detection window to record a full electropherogram.

FIG. 3 depicts a chromatography system rather than an electrophoresis system. This system is identical in configuration to that of the system of FIG. 2, except that the capillary 51 in this system is filled with a chromatographic separation medium such as a gel or a packed bed. The system depicted is one which uses a liquid carrier, which is pumped through the capillary by a conventional chromatography pump 52. The system otherwise performs and is operated in the same manner as described above for FIG. 2. A chromatography system counterpart to the configuration of FIG. 1 may likewise be constructed, and operated in an analogous fashion. In either case, the particular type of chromatography may vary widely. Examples are adsorption chromatography, gel-filtration chromatography, ion exchange chromatography and partition chromatography.

The following examples are offered for purposes of illustration only, and are intended neither to limit nor to define the invention in any manner.

EXAMPLE 1

A straight length of fused silica tubing, 540 mm in length with inner diameter of 0.075 mm, its outer surface coated with non-UV transparent polyimide, was used as the capillary. Sections of the polyimide coating at four locations along the length of the capillary were burnt off with an electrically heated tungsten wire. This created UV-transparent windows in the capillary at locations which were 12 cm, 17 cm, 27 cm and 37 cm, respectively, from the end of the capillary into which the sample was to be introduced. Each of these windows was approximately 2 mm in length. The inside of the tubing along the entire length, including the UV-transparent windows, was then coated with a monolayer of linear polyacrylamide to eliminate adsorption and electroendosmosis. The effectiveness of this coating was verified by the observation that no changes in migration velocities occurred over four weeks, during which time the capillary was stored at pH 11.

The fused silica capillary was mounted in a V-groove so that the capillary could rest in a fixed position relative to the beam of a light absorption detector, but could also be moved longitudinally. The V-groove was cooled by flowing water. A slit (transverse opening) in the V-groove was aligned with the detector beam, the slit being of a height approximately equal to the outer diameter of the capillary and of a width of 0.15 mm (in the longitudinal direction of the capillary, transverse to the path of the detector beam). Detection was achieved with an LKB/Pharmacia (Uppsala, Sweden) HPLC 2141 variable wavelength monitor, modified for on-tube solute detection at a wavelength of 260 mm. The electropherogram was recorded with an REC 61 Servograph recorder from Radiometer, Copenhagen, Denmark.

An electrophoretic separation of λ DNA was performed in the capillary. The separation medium in the capillary was TBE buffer (0.09M Tris, 0.09M boric acid and 0.002M ethylene diamine tetraacetic acid), pH 8.2. The λ DNA was injected into the capillary by electrophoretic means at 2000 V for 30 sec, and once injected, subjected to the same voltage for running the electrophoretic separation. These operating conditions and the arrangement of the UV-transparent windows had been selected on the basis of a previous determination that all peaks representing the λ DNA in the sample would pass one window before reaching the next.

The recording of the separation was begun with the first UV-transparent window of the capillary aligned with the V-groove opening, this being the window located 12 cm from the injection end of the capillary. When all peaks had passed the detector, the capillary was moved backward in the V-groove to place the second UV-transparent window in alignment with the V-groove opening. This was repeated until all peaks passing each of the four UV-transparent windows had been detected, integrated and recorded.

Figure 4:
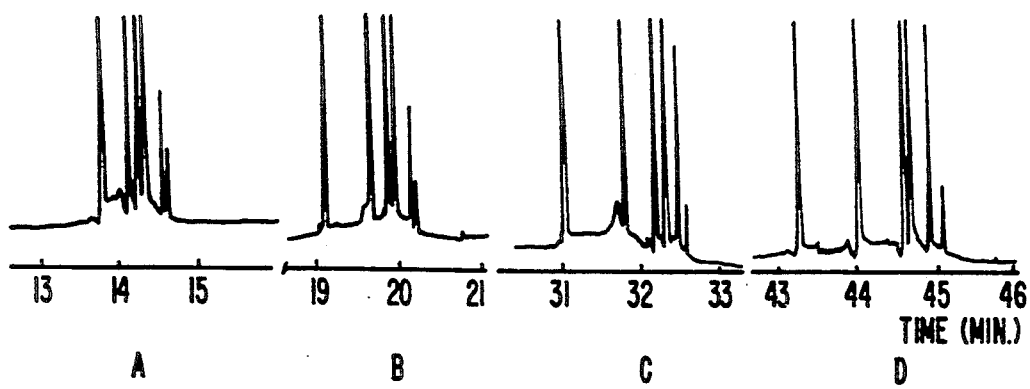
FIG. 4 is a trace from a strip chart recorder taken during an experimental run utilizing the system of FIG. 1.

Sections of the recorder trace are shown in FIG. 4, which demonstrates that the order and identity of the peaks is more complex than any single electropherogram would indicate.

EXAMPLE 2

A length of fused silica tubing, 580 mm in length with inner diameter of 0.05 mm, its outer surface coated with non-UV transparent polyimide, was used as the capillary. Sections of the polyimide coating were burnt off in the manner described in Example 1, creating UV-transparent windows at locations 4.0 cm, 14.0 cm and 44.0 cm from the injection end, each approximately 2 mm in length, and the inside of the tubing along the entire length, including the UV-transparent windows, was coated as in Example 1 with a monolayer of linear polyacrylamide.

Two loops were formed in the capillary, one between the first and second UV-transparent windows and one between the second and third, such that the portions of the capillary containing the windows placed parallel in a V-groove in the arrangement shown in FIG. 2, with the windows side by side. The loops were cooled by a fan, and the V-groove by flowing water. The V-groove contained a slit similar to that of the V-groove of Example 1, except that its height was slightly larger than the sum of the outer diameters of the three segments of the capillary. The width of the slit was 0.15 mm as before.

The same detector was used, together with a Spectra Physics SP 4270 Integrator, and detection was performed at 200 nm. The detector beam passed through all three UV-transparent windows simultaneously.

An electrophoretic separation was performed, using the following standard mixture of peptides obtained from Bio-Rad Laboratories, Inc. Hercules, Calif., U.S.A. (in order of elution):

1. Bradykinin
2. Angiotensin
3. α-Melanocyte stimulating hormone
4. Thyrotropin releasing hormone
5. Luteinizing hormone releasing hormone
6. [2–5] Leucine enkephalin
7. Bombesin
8. Methionine enkephalin
9. Oxytocin The separation medium used in the capillary was 0.1M sodium phosphate buffer, pH 2.5. Sample injection was achieved electrophoretically at 8000 V for 10 sec, and the running voltage was also 8000 V.

Figure 5:
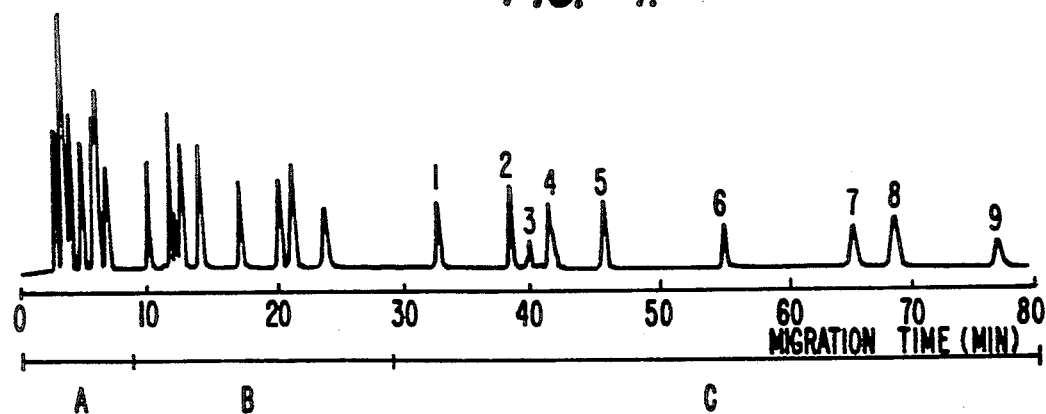
FIG. 5 is a trace from a strip chart recorder taken during an experimental run utilizing the system of FIG. 2.

The recorder trace is shown in FIG. 5, and three repetitions of the elution sequence are identified. The first repetition is indicated by the letter "a" in the trace, and represents the detector response to solutes passing the window at the 4.0 cm location; the second repetition is indicated by "b" and represents the window at the 14.0 cm location; and the third repetition is indicated by "c" and represents the window at the 44.0 cm location. The component number is placed above each peak in the third repetition. In the elution sequence in each of these repetitions, bradykinin, luteinizing hormone releasing hormone, [2-5] leucine enkephalin and oxytocin are identified as peaks 1, 5, 6 and 9, respectively, based on the known elution behavior of the standard mixture.

Integrated peak areas are listed in Table 1 below. To compensate for variations in variations in light intensity over the cross section of the detector UV beam and for other factors such as variations in the diameter of the capillary from one window to the next, the peak areas have been normalized relative to bradykinin.

TABLE 1
RELATIVE PEAK AREAS AT DIFFERENT DETECTION POINTS

| Window Location | Peptide | | | |
|---|---|---|---|---|
| | Bradykinin | Luteinizing Hormone Releasing Hormone | [2-5] Leucine Enkephalin | Oxytocin |
| 4.0 cm | 1.00 | 1.30 | 0.91 | 0.90 |
| 14.0 cm | 1.00 | 1.28 | 0.94 | 0.91 |
| 44.0 cm | 1.00 | 1.33 | 0.94 | 0.90 |

Figure 6:
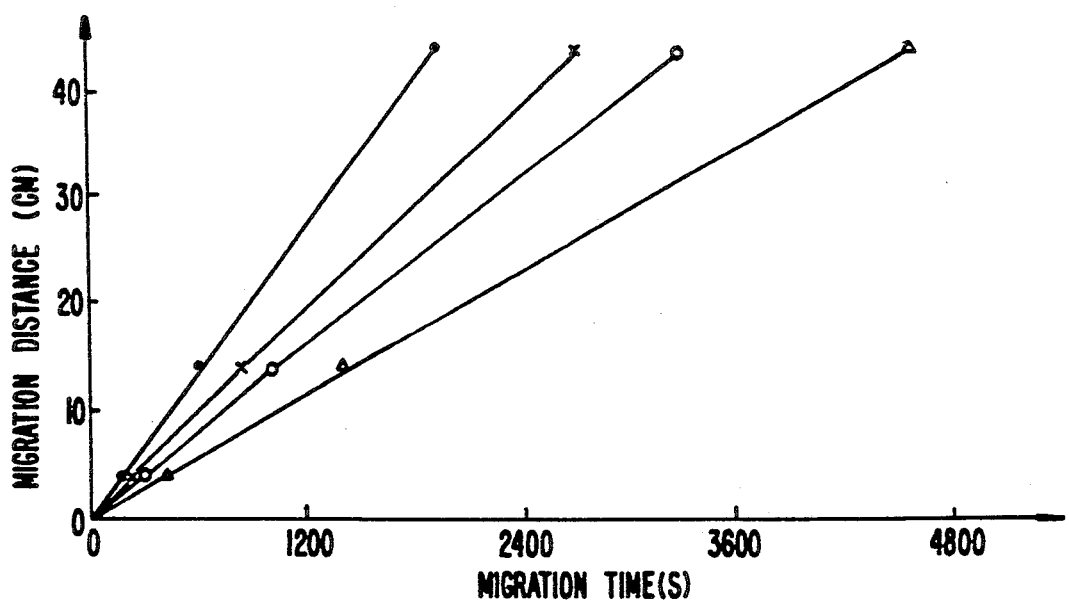
FIG. 6 is a plot of migration distance vs. time for four peptides taken from the trace of FIG. 5.

In FIG. 6, the migration distance in centimeters (i.e., the distance of the window from the injection end of the capillary) is plotted against the time in seconds at which each peak appeared at the detector. The filled circles in the Figure represent bradykinin; the x's represent luteinizing hormone releasing hormone; the open circles represent leucine enkephalin; and the triangles represent oxytocin. The points fall in straight lines, indicating that mobility values (migration velocity in cm/sec divided by field strength in volts/cm) are readily determined to a high degree of accuracy. These values are listed in Table 2 below.

TABLE 2
MOBILITY VALUES FOR FOUR PEPTIDES

| Peptide | Mobility × $10^{-4}$ (cm$^2$s$^{-1}$V$^{-1}$) |
|---|---|
| Bradykinin | 1.61 |
| Luteinizing Hormone Releasing Hormone | 1.17 |
| [2-5]Leucine Enkephalin | 0.96 |
| Oxytocin | 0.69 |

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

What is claimed is:

1. A method for obtaining a plurality of solute peak patterns representing successive stages of a continuous separation of solutes by a separation process selected from chromatographic and electrophoretic separations performed in a separation medium retained in a capillary, said method comprising detecting, with a single detector, variations in light absorptivity as a function of time at a plurality of locations spaced apart along the length of said capillary.

2. A method for determining values representative of the mobilities and relative amounts of solutes undergoing electrophoretic separation through a separation medium in a capillary, said method comprising:
   (a) with a single detector, detecting variations in light absorptivity by said separation medium as a function of time at a plurality of detection points spaced apart along the length of said capillary;
   (b) at each said detection point, identifying peaks in the variations in light absorptivity thus detected, and a sequence in which said peaks occur which is substantially the same at all said detection points;
   (c) for each peak in said sequence, averaging among all said detection points the distance traveled by said peak to said detection point divided by the time taken by said peak to reach said detection point; and
   (d) for each peak in said sequence, averaging among all said detection points the areas defined by peaks at the same position in said sequence.

3. A method for obtaining a plurality of solute peak patterns representing successive stages of a continuous separation of solutes by a separation process selected from the group consisting of chromatographic and electrophoretic separations performed in a separation medium retained in a capillary, as said solutes are migrating in a direction of migration in said capillary, said method comprising:
   (a) aligning a first location in said capillary with a light absorptivity detector, and obtaining a first solute peak pattern by detecting variations in light absorptivity by said separation medium as a function of time at said first location;
   (b) displacing said capillary relative to said detector to align therewith a second location further along the length of said capillary in said direction of migration, and obtaining a second solute peak pattern by detecting variations in light absorptivity as a function of time at said second location; and
   (c) repeating step (b) at a sufficient number of locations to achieve said plurality of solute peak patterns.

4. A method in accordance with claim 3 in which said separation process is electrophoresis, and said solute peak patterns are electropherograms.

5. A method in accordance with claim 4 further comprising:
   (d) for each of said electropherograms, identifying peaks therein and a sequence in which said peaks occur, said sequence being substantially the same in each of said electropherograms;
   (e) for each peak in said sequence, averaging among all said electropherograms the distance traveled by said peak to the location at which said electropherogram is obtained divided by the time taken by said peak to reach said location; and
   (f) for each peak in said sequence, averaging among all said electropherograms the areas defined by peaks at the same position in said sequence.

6. A method in accordance with claim 4 in which said capillary is a length of fused silica whose outer surface is coated with polyimide in a substantially continuous manner except for discontinuities at each of said locations aligned with said light absorptivity detector in steps (a) and (b).

7. A method in accordance with claim 6 in which the interior surface of said capillary is coated with a substance which suppresses adsorption and electroendosmosis and is transparent to ultraviolet light.

8. A method in accordance with claim 7 in which said substance is a member selected from the group consisting of linear polyacrylamide, dextran and methyl cellulose.

9. A method in accordance with claim 4 in which said capillary has an internal diameter of from about 5 microns to about 300 microns.

10. A method in accordance with claim 4 in which said capillary has an internal diameter of from about 20 microns to about 100 microns.

11. A method for obtaining a plurality of solute peak patterns representing successive stages of a continuous separation of solutes by a separation process selected from the group consisting of chromatographic and electrophoretic processes, said method comprising:
  (a) subjecting said solutes to conditions promoting said separation process in a separation medium retained in a capillary, said capillary being looped at least once to place a plurality of locations along the length of said capillary defined as detection points in sufficient proximity to each other that all such detection points intercept a single detection beam of a light absorption detector, each pair of detection points separated by at least one loop of said capillary; and
  (b) detecting variations in the absorption of light from said detection beam by said separation medium as a function of time, caused by the migration of said solutes through said separation medium past said detection points.

12. A method in accordance with claim 11 in which said separation process is chromatography, and said solute peak patterns are chromatograms.

13. A method in accordance with claim 11 in which said separation process is electrophoresis, and said solute peak patterns are electropherograms.

14. A method in accordance with claim 13 further comprising:
  (c) identifying peaks in the variations thus detected, and grouping said peaks into electropherograms, one corresponding to each detection point;
  (d) identifying a sequence in which said peaks occur in each of said electropherograms, said sequence being substantially the same in each of said electropherograms;
  (e) for each peak in said sequence, averaging among all said electropherograms the distance traveled by said peak to the detection point at which said electropherogram is obtained divided by the time taken by said peak to reach said detection point; and
  (f) for each peak in said sequence, averaging among all said electropherograms the areas defined by peaks at the same position in said sequence.

15. A method in accordance with claim 13 in which said capillary is a length of fused silica whose outer surface is coated with polyimide in a substantially continuous manner except for discontinuities at each of said detection points.

16. A method in accordance with claim 15 in which the interior surface of said capillary is coated with a substance which suppresses adsorption and electroendosmosis and is transparent to ultraviolet light.

17. A method in accordance with claim 16 in which said substance is a member selected from the group consisting of linear polyacrylamide, dextran and methyl cellulose.

18. A method in accordance with claim 11 in which said capillary has an internal diameter of from about 5 microns to about 300 microns.

19. A method in accordance with claim 11 in which said capillary has an internal diameter of from about 20 microns to about 100 microns.

20. A method in accordance with claim 11 in which said detection beam is emanated from a light source and said variations in light absorption are detected by a light detector, and said detection points of said capillary, said light source and said light detector are all temperature controlled.

* * * * *